United States Patent [19]

Scheller

[11] Patent Number: 4,749,865
[45] Date of Patent: Jun. 7, 1988

[54] APPARATUS FOR DETERMINING AN OPTIUM SUNSCREEN FACTOR AT ANY GIVEN TIME

[76] Inventor: Klaus Scheller, Konigsteiner Str. 47, D 6232 Bad Soden a. TS, Fed. Rep. of Germany

[21] Appl. No.: 833,080

[22] Filed: Feb. 25, 1986

[30] Foreign Application Priority Data

Feb. 26, 1985 [DE] Fed. Rep. of Germany ....... 3506690

[51] Int. Cl.⁴ ............................ G01J 1/00; G01J 1/42
[52] U.S. Cl. ..................................... 250/338; 250/372
[58] Field of Search ........................... 250/372, 338 R; 364/414

[56] References Cited

U.S. PATENT DOCUMENTS 3,967,124  6/1976 Strutz ................................. 250/372
4,428,050  1/1984 Pellegrino et al. ................. 250/372

Primary Examiner—Janice A. Howell
Attorney, Agent, or Firm—Volpe and Koenig

[57] ABSTRACT

An apparatus for determining an optimum sunscreen factor at any given time for the purpose of selecting a sunscreen suitable for protecting the skin, located in a housing is an indicator for the sunscreen factor, an energy source, preferably a battery, an on-off switch, as well as a sensor responsive to the tanness of the skin and provided with a pick-up which is connected via an electronic evaluation circuit with the indicator.

19 Claims, 3 Drawing Sheets

APPARATUS FOR DETERMINING AN OPTIUM SUNSCREEN FACTOR AT ANY GIVEN TIME

BACKGROUND OF THE INVENTION

The invention concerns an apparatus for determining an optimum sunscreen factor at any given time for the purpose of selecting a sunscreen preparation suitable for protection of the skin.

During sunbathing, but also under irradiation devices, e.g., sunlamps or the like, many people confront the problem of protecting their skin from the damaging effects of ultraviolet radiation while, on the other hand, still attaining a healthy tanning of the skin in a relatively short period of time.

Many sunscreens exercise over against UV radiation a filtering action. The degree of filtration corresponds to a sunscreen factor, for example, 1–15. These numbers are intended to put the sunscreen user in a position to select a sunscreen with the right factor.

In order to facilitate this selection, one has recently begun announcing on a daily basis as a "sunburn warning", for example, at public beaches on the Adriatic Sea the UV radiation and the corresponding sunscreen factor. Here, one can make good use of a device known as a "Sun-Timer", which, like an exposure meter, collects the UV radiation and converts it electronically into measured values with which the sunscreen factors are coordinated (periodical: HOR ZU, no. 87/1984).

To be sure, this announcement of sunscreen factors, which are also given on the packages of sunscreens, makes things easier for a lot of people. Disadvantageous, however, is the fact that one does not take into consideration the individual state of the skin. This state is usually evaluated on the basis of opinion and superficial inspection.

The parameters to be considered when selecting a proper sunscreen are not only the objective measurement of UV radiation, but also an evaluation of the current state of the skin.

This is basically determined by the skin's subjective, biological nature, for example, light and transparent or brown (pigmented) and opaque and additionally by its state as a result of sunlight or UV radiation. Both factors are responsible for the skin's tanning value at a given point in time. Only the most precise possible determination of this value can provide a reliable basis for the proper selection of the sunscreen factor.

It is also known to use color scales combined with the sunscreen factors, for comparison with the current color of the skin. Thus, a method and device for photocolorimetrically determining the tanning degree of different skin types (German patent No. 20 58 579), which permits photometrically ascertaining the degree of tanning of different human skin types and the establishment of a tanning scale from 0.0% to 100%. This device is designed such that it requires the comparison with one of many color tones (to which a number is assigned in each case) in measuring the degree of tanning of the skin. The device possesses a number of color-tone carriers, either colored plastic cards rotatable around a common axis or sections of a plastic disk. It has been found, however, that these color comparisons can not lead, in practice, to sufficiently reliable selection of the sunscreen necessary in a given case. This is because the color scales do not take into consideration the individual subjective character of a skin.

SUMMARY OF THE INVENTION

In comparison, the present invention is aimed at providing an electrical device with which one can determine the required sunscreen factor. Permitting selection of the right sunscreen as a function of the individual properties of the skin and its current state.

It was found that this problem can be solved in a simple manner through an electrical sensor responding to skin tanness, with a reflection photocell operating in the red spectral range and including a light source and at least one photometric element. Preferably a photometric resistor, is positioned in a housing together with an energy source, a battery, and an on-off switch, the sensor being connected via an electronic evaluation circuit with the ability to indicate the sunscreen factor.

As a result, the present invention makes possible not only a practical determination of the individually required sunscreen factor, but attains in an especially advantageous manner a situation where one can also simultaneously determine with the apparatus the tanness of the skin. Therefore, a given persons skin could be monitored or the tanned skin of others could be compared.

As a result of the sensor operating in the red spectral range, the apparatus according to the present invention is in a position to assess skin reddened by the sun or even as a result of other skin irritation. The sensor produces red skin measured values which also occur with white skin. Both measured values, that from red skin and that from white skin, are processed by an electronic evaluation circuit such that the indicator shows that sunscreen factor which is necessary for unexposed (i.e., white) sensitive skin.

The apparatus reacts otherwise with tanned or brown skin exhibiting no red component. It indicates the corresponding tanness and sunscreen factor.

With a mixture of brown and red pigments, i.e., with a skin which is both tanned as well as irritated and reddened, the red component is assessed and becomes a part of the measured value. The indicator points to the sunscreen factor corresponding to the reddening of the skin.

The electronic evaluation circuit according to the present invention has the ability to establish a lower threshold corresponding to the tanness of an extremely white skin and has the ability to establish an upper threshold value corresponding to the tanness of an extremely brown skin. As a result, it is possible to arrive at useful and objective data for sunscreen factors in spite of considering different skin properties.

The embodiments in the examples of the invention use a sensor containing an artificial light source, which provides the same light for all of the measurements.

The equipment can be contained in any appropriately shaped housing, for example, oval, round, or rectangular cross-section. One can use as an on/off switch either a hand-actuated switch on the housing with a stationary and a moving contact or a skin-contact switch, whose contacts are positioned opposite to each other along two lateral edges of the measuring window.

The electronic evaluation circuit includes an analog/digital converter with a subsequent digital translator for the tanness and the associated sunscreen factor. Provided in this device is a two-position digital indicator for tanness and a digital indicator for the sunscreen factor.

The electronic evaluation circuit may also be connected via a regular control circuit to a string of light-emitting diodes.

The apparatus according to the present invention can also include a connection for a chain or neck-strap. Using commercially attainable circuit elements, it is possible to build the apparatus to be somewhat larger than a normal pocket-watch. Upon use of a special so-called microchip, the size of the overall apparatus is reduced to that of a conventional wristwatch.

DESCRIPTION OF THE PREFERRED EMBODIMENT

Figure 1:
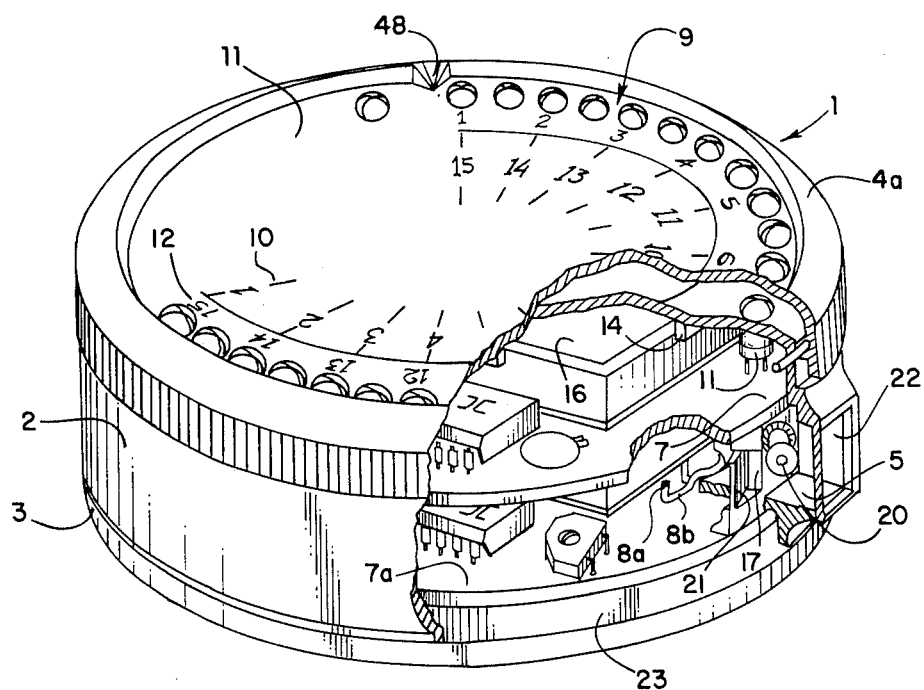
FIG. 1 a perspective partial view of a preferred embodiment of the invention.

FIG. 1 shows a perspective view of a housing 1, whose diameter runs approximately between 5 and 8 cm and whose height amounts to about 1-3 cm.

The cylindrical housing 1 possesses a side wall 2, a lower housing cover 23, as well as an upper transparent rotatable cover 4a. Positioned below this cover 4a are two scales. A first inner scale 10 gives the sunscreen factors 1 through 15. The second scale 12 has numerical data in any desired graduation for giving the tanness of the skin. The numbers of the first scale 10 are associated with those of the second scale 12. The side wall 2 of the housing ends in lower edge 3. There can be positioned in the side wall 2 the hand actuator of an on-off switch generally labelled 8, belonging to which (FIG. 2) are a movable contact 8b and a stationary contact 8a.

In a manner not shown in FIG. 1, the housing 1 can be equipped with a hook for attachment of a neck-chain or a cord.

The rotatable transparent cover 4a is located in the upper region of the housing 1. The lower housing covering 23 can be screwed, glued, or clamped in any known fashion with side wall 2, in order to make it possible to access the interior of the housing 1.

Figure 4:
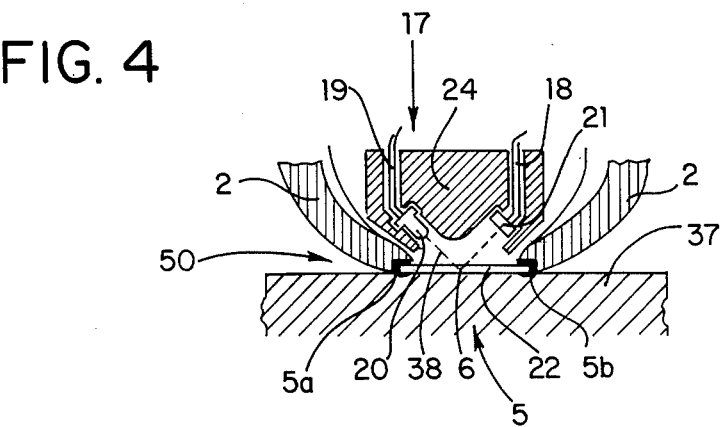

Without affecting the scope of the invention, one can use any other type of on-off switch. FIG. 4 shows, for example, an on-off switch combined with a measuring window 22 positioned in side wall 2. This switch is designed as a skin-contact switch 5, with contacts 5a and 5b. The fixed contacts 5a and 5b are lateral edges of the measuring window 22. Positioned behind this window, in analogy to FIG. 2, is the holder 24 for a reflection photocell 17 designed as a pick-up.

Below the transparent cover 4a, one can see a scale support 14, which is joined to a plate 7. Provided on the scale support 14 are the two scales 10 and 12, which, in the preferred embodiments, are applied to pressure-sensitive-adhesive paper and glued to the scale support 14. The advantage of readily removable scales 10 and 12 is that the apparatus can be quickly converted to other scale divisions or can be provided during manufacture with different scales during manufacture. However, scales 10 and 12 can also be directly applied to the scale support 14, for example, the scales can be printed thereon. They can also be cast integrally with the scale support 14.

Figure 2:
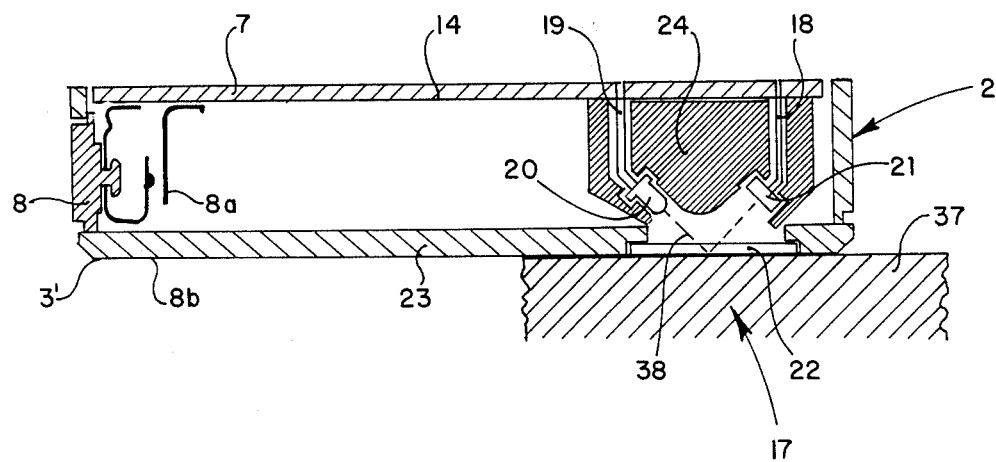
FIG. 2 a partial section through an alternative embodiment

Between the scale support 14 and the lower housing cover 23, preferably in the edge area, the reflection photocell 17 can be positioned as the pick-up, as shown in FIG. 2. The reflection photocell 17 consists of a light-emitting diode 20 and a photometric element or photometric resistor 21, both of which are oriented such that a light beam 38 emitted by the diode is directed through the measuring window 22 onto an area of the skin 37 and can be reflected by the latter. The light-emitting diode 20 and the photometric resistor 21 can sit on a common holder 24 positioned opposite to the measuring window 22. The light-emitting diode 20 is supplied with current via leads 19, whereas the signals from the photometric element or photometric resistor 21 are fed via leads 18 to a subsequently described electronic circuit.

The energy source, for example, is a commercial battery 16, which sits in the usual fashion in a known clamping holder.

An indicator includes a series of light-emitting diodes 9 next to scales 10 and 12 in housing 1. The light-emitting diodes 11 of this series 9 are arranged on the plate 7.

Plate 7 and a further plate 7a hold the individual electronic circuit components. Clearly recognizable is the integrated unit 50 consisting of measuring window 22 and skin contact switch 5, which also includes the light-emitting diode 20 of the pick-up and a photometric element or photometric resistor 21. According to FIG. 4, the measuring window 22 can be covered by a disk 6 of screen material.

Figure 3:
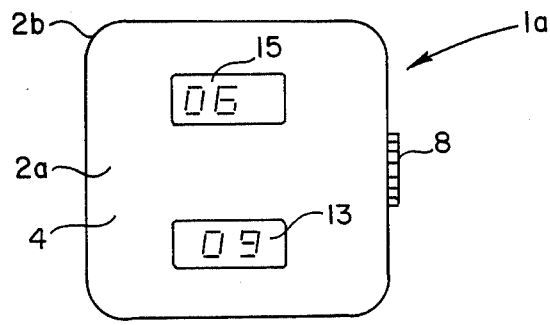
FIG. 3 diagram of a top view looking down on the housing of a second embodiment, FIG. 4 a partial section for representation of a skin-contact switch, FIG. 5 a simplified partial block diagram of the electronic evaluation circuit, FIGS. 6, 7, and 8 block diagrams for individual embodiments.

FIG. 3 shows a housing 2a of rectangular cross-section, with an appropriate side wall 2b and a transparent cover 4. Clearly recognizable is the on/off switch 8, which, without affecting the scope of the invention, can also be designed as a skin contact switch 5 according to FIG. 4. Digital indicators 13 and 15 are provided in the transparent cover for indicating both tanness and sunscreen factor.

Figure 5:
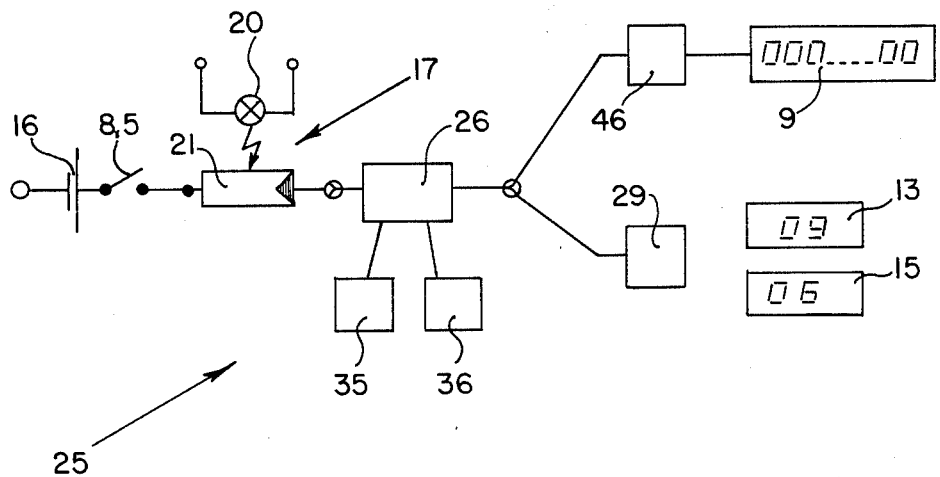

FIG. 5 shows an electronic circuit arrangement 25 in which a measured value can be produced, electronically processed, and displayed.

Recognizable in series with the energy source 16 is either of the on-off switches 5 or 8. Skin contact switch 5 forms an integrated unit 50 together with the measuring window 22, as shown in FIG. 4.

Recognizable behind the on-off switches 5 or 8 is the pick-up 17, which contains the photometric element or photometric resistor 21, which sits opposite a light-emitting diode 20, which can be, for example, a red light-emitting diode, preferably with a wave length between 600 nm and 750 nm or even a miniature incandescent lamp. If a normal miniature incandescent lamp is used as the light source 20, the measuring window 22 can also be covered by a spectral filter, preferably a dereflected line filter in the red spectral range.

The pick-up 17 is connected to an electronic evaluation circuit 26, to which are connected an arrangement 35 for establishing a lower threshold value and an arrangement 36 for establishing an upper threshold value.

In the embodiment of FIG. 1, the indicator is a series of light-emitting diodes 9, which is linked via a control circuit 46 with the electronic evaluation circuit 26.

The two-position digital indicators 13 and 15 in the embodiment of FIG. 3 are connected via a digital translator 29 to the electronic evaluation circuit 26.

Figure 6:
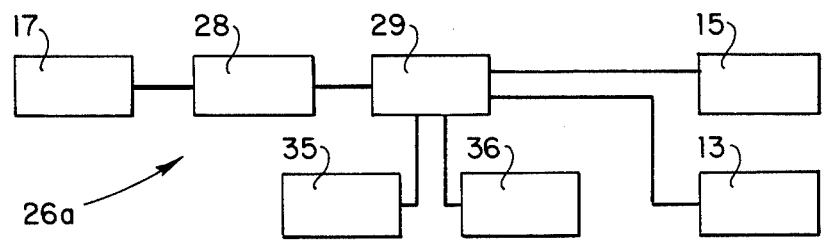

FIG. 6 shows a block diagram for an evaluation circuit 26a for digital indicators with an A/D converter 28, preferably with a sample-and-hold circuit, which is connected to the pick-up 17. The digital translator 29 connected to the A/D converter 28 is connected through the digital indicators 13 and 15 and to the arrangements 35 and 36 for establishing an upper and a lower threshold value.

All of the embodiments of the invention exhibit an arrangement 35 for establisning an upper threshold value and an arrangement 36 for establishing a lower threshold value. With arrangement 35, a lower threshold value can be established corresponding to the tanness of an extremely white skin, whereas, with arrangement 36, an upper threshold value can be established for the tanness of an extremely brown skin.

Figure 7:
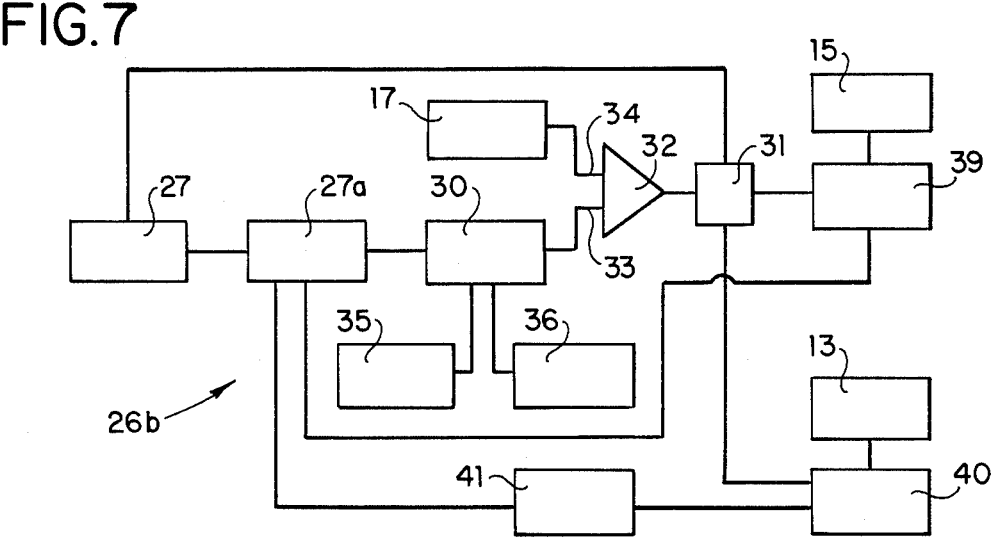

In the embodiment of an electronic evaluation circuit according to FIG. 7, the arrangements 35 and 36 are formed as resistors for the reference voltage producer 30. In particular, shift register or counter 27a dries the reference voltage producer 30, which consists of resistors connected to the outputs of the counter or the shift register 27. These resistors of the reference voltage producer 30 are dimensioned and connected such that a staircase curve with preferably 64 voltage steps lies at the first input 33 of a comparator 32. As soon as one of these voltages steps corresponds to the voltage fed to the second input 34 of the comparator 32 by the pick-up 17, the comparator switches in known fashion via a measured-value holding circuit 31 to a indicator driver 39 with decimal coder for digital indicator 15 and to a indicator drive 40 with decimal coder for decimal indicator 13.

Commercial circuit components are employed for elements 27, 27a, 28, 29, 30 as well as 32, 33, and 34 and arrangements 35 and 36, but also for the measured-value holding circuit 31.

Figure 8:
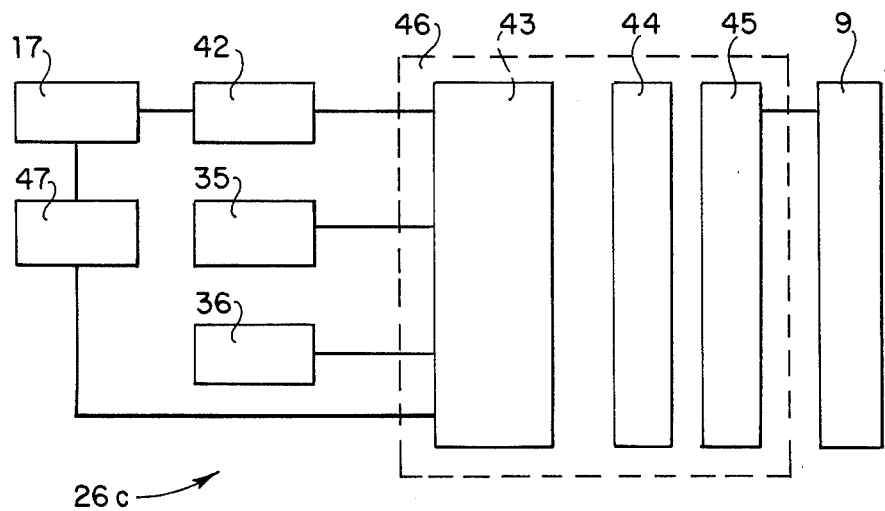

The electronic evaluation circuit 26c for the known series of light-emitting diodes 9 is shown in FIG. 8. It consists of a unit 46 with a circuit 43 in which a reference voltage producer 30 and a comparator 32 are combined. Connected to circuit 43 is a logic circuit 44 for controlling the series of light-emitting diodes 9 via a drive circuit 45. Circuit 43 is connected via an automatic holding/cut-out circuit 47 with defined holding time with pick-up 17. Additionally connected to circuit 43 is a circuit 42 for holding an analog value. Unit 46 is formed by the commercial ICU 1096 of Telefunken-Elektronik.

I claim:

1. An apparatus for measuring the degree of skin tanness and determining an optimum sunscreen factor at any given time for the purpose of selecting a sunscreen suitable for protecting the skin comprising:
   a housing including an energy source,
   an electrical sensor powered by said energy source and being responsive to the degree of skin tanness, said electrical sensor including a reflection photocell operating in the red spectral range,
   said reflection photocell including a light source and at least one photometric element,
   an electrical evaluation circuit responsive to said electrical sensor for determining the optimum sunscreen factor, and
   an indicator for displaying said determined optimum sunscreen factor.

2. The apparatus of claim 1, wherein said electronic evaluation circuit includes means for establishing a lower threshold value corresponding to the tanness of extremely white skin and means for establishing an upper threshold value corresponding to the tanness of an extremely brown skin.

3. The apparatus of claim 1, wherein a measuring window is located in a section of said housing, said measuring window facing an area of the skin to be investigated, and said electrical sensor being located opposite said measuring window inside said housing.

4. The apparatus of claim 3, further including an on/off switch for activating said apparatus and wherein said measuring window and said on/off switch are integrated into one structural unit.

5. The apparatus of claim 4, wherein said on/off switch includes contacts positioned along two opposing edges of said measuring window.

6. The apparatus of claim 1, wherein said light source is a red light-emitting diode with a wave length of 600 to 750 nm.

7. The apparatus of claim 6, wherein said light source is a miniature incandesant lamp.

8. The apparatus of claim 3, wherein said measuring window is closed off by a dereflection line filter in the red spectral range.

9. The apparatus of claim 1, wherein said light source and said photoresistor are located in a common holder.

10. The apparatus of claim 1, wherein said electronic evaluation circuit includes an analog/digital convertor and a digital translator for transmitting said optimum sunscreen factor signal to said indicator and a degree of tanness signal to a second indicator, each of said indicators being of a two-position digital type.

11. The apparatus of claim 10, wherein said two-position digital indicators include either liquid crystals or light-emitting diodes, said indicators are driven by an indicator drive with decimal decoder.

12. The apparatus of claim 1, wherein said electronic evaluation circuit is connected via a control circuit to a series of light-emitting diodes.

13. The apparatus of claim 12, wherein an analog measured-value holding circuit is provided between said control circuit and said electrical sensor.

14. The apparatus of claim 13, wherein an automatic cut-off circuit is provided between said electrical sensor and said control circuit.

15. The apparatus of claim 12, wherein said series of light-emitting diodes is adapted to the peripheral shape of said housing, said series of light-emitting diodes include a first scale being associated with sun screen factors and a second scale being associated with tanness values of the skin area.

16. The apparatus of claim 1, wherein said housing includes an upper transparent cover and said indicator is located below said upper transparent cover.

17. The apparatus of claim 16, wherein said upper transparent cover is rotatably supported and includes a mark for indicating a measured value.

18. The apparatus of claim 5, wherein said scales include pressure sensitive adhesive material removably located on a scale support.

19. The apparatus of claim 3, wherein said measuring window is closed off by a material selected from a group consisting of dereflecting glass, dereflecting transparent plastic, and a disc of screen material.

* * * * *

UNITED STATES PATENT AND TRADEMARK OFFICE
CERTIFICATE OF CORRECTION

PATENT NO. :  4,749,865
DATED      :  June 7, 1988
INVENTOR(S) : Klaus Scheller

It is certified that error appears in the above-identified patent and that said Letters Patent is hereby corrected as shown below:

Column 4, line 33, after the word "pick-up" insert --17--.

Claim 38, column 6, line 61, delete "5" and insert --15--.

Signed and Sealed this

First Day of November, 1988

Attest:

DONALD J. QUIGG

*Attesting Officer*    *Commissioner of Patents and Trademarks*